United States Patent [19]

Bitterly

[11] Patent Number: 4,869,250
[45] Date of Patent: Sep. 26, 1989

[54] LOCALIZED COOLING APPARATUS

[75] Inventor: Jack G. Bitterly, Woodland Hills, Calif.

[73] Assignee: Thermacor Technology, Inc., Newbury Park, Calif.

[21] Appl. No.: 709,093

[22] Filed: Mar. 7, 1985

[51] Int. Cl.⁴ .............................................. A61F 7/00
[52] U.S. Cl. ................................... 128/400; 128/403
[58] Field of Search ............................. 128/399–400, 128/402–403; 62/55, 52, 149, 504, 62, 534–535, 440, 419; 122/407

[56] References Cited

U.S. PATENT DOCUMENTS

| | | | |
|---|---|---|---|
| Re. 30,317 | 7/1980 | Lubbers et al. | 128/635 |
| 2,551,650 | 5/1951 | Urbach | |
| 2,982,132 | 5/1961 | Mendlowitz | |
| 3,216,492 | 11/1965 | Weaver | 128/400 X |
| 3,479,838 | 11/1969 | Bitterly | |
| 3,587,577 | 6/1971 | Smirnov et al. | 128/402 X |
| 3,894,213 | 7/1975 | Agarwala | 128/400 X |
| 4,026,299 | 5/1977 | Sauder | 128/400 |
| 4,174,619 | 11/1979 | Tocha | 62/55 X |
| 4,175,543 | 11/1979 | Suzuki et al. | 128/736 |
| 4,191,197 | 3/1980 | Benzinger | 128/736 |
| 4,228,805 | 10/1980 | Rosen et al. | 128/691 |
| 4,336,695 | 6/1982 | Ceolotto | 62/504 |
| 4,348,873 | 9/1982 | Yamauchi et al. | 62/52 X |
| 4,459,825 | 7/1984 | Crouch | 62/440 X |
| 4,483,021 | 11/1984 | McCall | 128/399 X |
| 4,523,594 | 6/1985 | Kuznetz | 128/399 X |
| 4,563,879 | 1/1986 | Hama et al. | 62/504 X |
| 4,573,327 | 3/1986 | Cochran | 62/504 X |

FOREIGN PATENT DOCUMENTS 0044112 3/1980 Japan ......................................... 62/52

Primary Examiner—Kyle L. Howell
Assistant Examiner—Angela D. Sykes
Attorney, Agent, or Firm—Poms, Smith, Lande & Rose

[57] ABSTRACT

The flexible cooling fabric has an injector that is flat so that it can be maintained unobtrusively within the cooling fabric. The injector has a flat electromagnetic coil which surrounds an injection chamber. The chamber receives pressurized fluid, but a spring-biased plunger closes the outlet openings to the chamber. The fluid of the electromagnetic coil tends to center the plunger within the chamber to uncover the outlet openings, and the fluid flows toward a membrane which is against the skin or other object to be cooled. The refrigerant gas boils due to the heat flux from the skin, and this results in rapid and efficient cooling. The present invention also includes a system for recycling spent refrigerant gas. The gas is collected in a volume absorber, and only when the volume inside of the absorber reaches a predetermined maximum does the compressor operate to relieve the pressure in the volume absorber by compressing the spent gas and injecting it back into the storage tank. The compressor operates efficiently because it only runs intermittently when the pressure in the volume absorber is above predetermined limits, but the tank continues to supply refrigerant to the injector when the compressor is not operating.

25 Claims, 3 Drawing Sheets

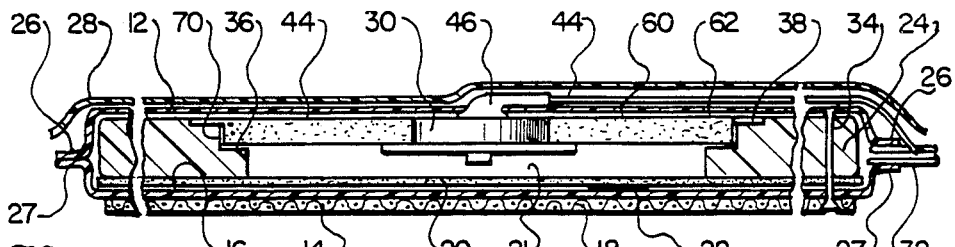
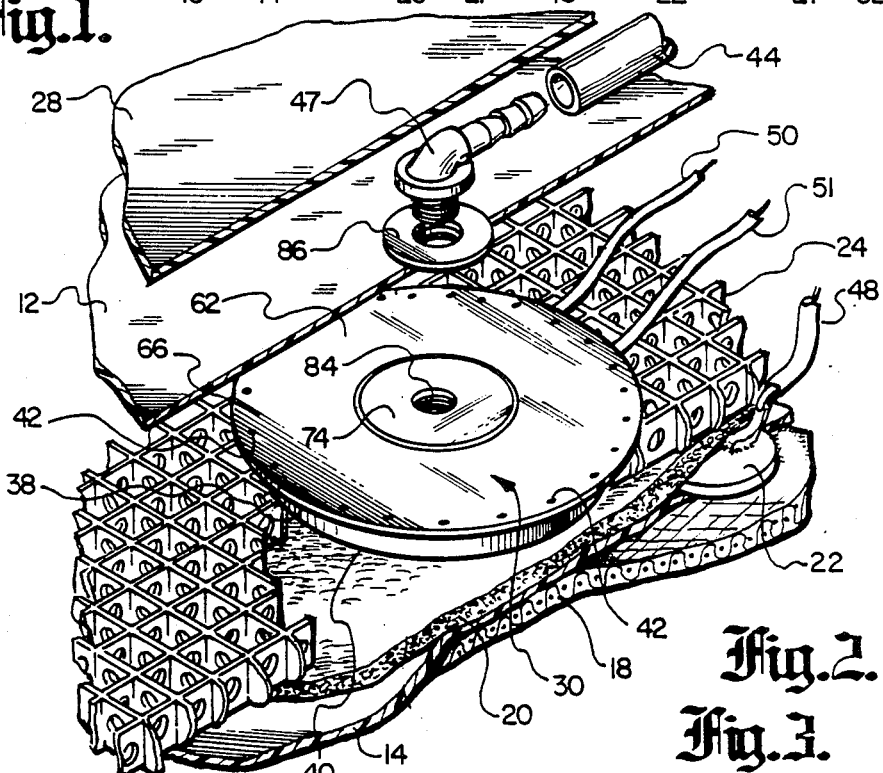
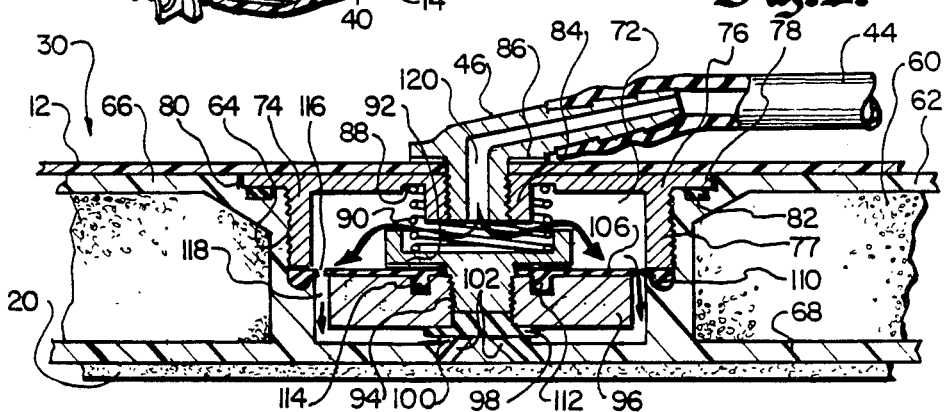

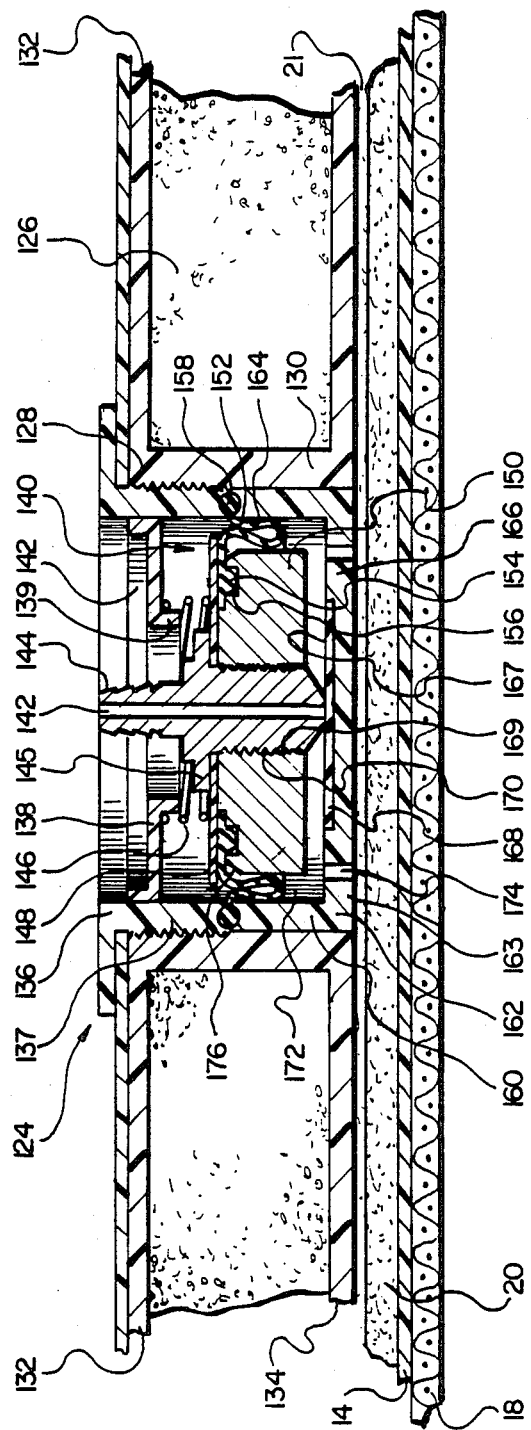

LOCALIZED COOLING APPARATUS

BACKGROUND OF THE INVENTION

1. Related Patents and Applications

This application is an improvement over applicant's U.S. Pat. No. 3,479,838 (1969) entitled "Cooling Material". It is also a continuation-in-part of applicant's pending application Ser. No. 383,004 entitled "Method and Apparatus for Monitoring and Diagnosing Peripheral Blood Flow" and Ser. No. 673,509 entitled "Blood Flow Monitoring Device" now Pat. No. 4,569,335 (1986).

2. Field of the Invention

This invention relates to fabric or garments for localized cooling of a person's skin or of another object.

3. Need For the Invention

Localized cooling is extremely useful in many applications of which the following examples are but a few. Industrial workers in high temperature environments such as foundries and agricultural workers in the desert are exposed to high temperatures. At high temperatures, workers fatigue more easily and productivity decreases. It is impractical to air condition an entire foundry; farm laborers also cannot work in air conditioned environments. Therefore, it is desirable to cool these workers' skin. Peak efficiency and comfort may still be maintained if only the trunk or trunk and head are cooled. The limbs, which have a large surface area to volume ratio, naturally radiate enough heat. As a matter of fact, amputees often find it difficult to radiate sufficient heat from their bodies even at low levels of activity in environments that would be relatively comfortable for persons with all of their limbs. Thus, cooling of the trunk of amputees is another application of the present invention.

Some persons are exposed to heat from one localized source. For example, a race car driver with a rear engine car is exposed to high heat quantities at his or her back. For racing efficiency, it is not practical to air condition the driver compartment, and added insulation adds undesirable weight to the vehicle. Moreover, race drivers usually wear protective clothing for fire and crash protection that tends to retain body heat. For them, localized cooling, which might concentrate on cooling the driver's back, would be most helpful.

Surgical patients, especially those undergoing open heart surgery, often must be cooled to lower metabolism and blood flow. This is normally done with ice, but the ice needs replenishing, and it is more difficult to control the actual temperature.

As another example, one can cool a small area only and give the user the perception of comfort. For example, a cool head band or cap worn during strenuous exercise may allow the user to feel comfortable even though the rest of the body is above normal temperature.

Localized applications of cooling are not confined to humans. Electronics components, for example, heat up. Although they may be ventilated with outside air, as more circuitry is confined to a smaller area, outside air may be insufficient or at too high a temperature to cool the components. It would be useful, therefore, to provide a small device that could be inserted into an electronic device merely for the purpose of cooling localized areas. There may also be certain chemical processes which would benefit from localized cooling.

Localized cooling can be obtained by refrigerated air conditioning, but in many of the applications just discussed, that type of air conditioning is not practical because of weight, power consumption, restrictions on mobility and/or other reasons.

4. Prior Art

Applicant's Pat. No. 3,479,838 teaches a cooling fabric primarily for use in space. The cooling fabric had several layers, and water is injected between some of the layers. In the vacuum of outer space, water boils at skin temperature, and heat from the skin causes the water to boil. Heat exchange during a change of phase is great, and the resultant boiling caused the skin to cool. The device does not work at or near standard temperatures (body or environment) and pressure.

There are garments with channels for carrying cooling water. Applicant's earlier patents suggest the use of additional cooling liquid to augment the cooling from the boiling water. That type of system is prohibitive for everyday use on the ground because of weight and power requirements. Recirculating water must be cooled somehow unless one has access to cooling water that can be expelled after use or refrigerated at the expense of energy. Also, if the garment uses cold water or other liquid, the liquid flows through tubes, which must have thick enough walls to avoid kinking. These tubes have poor surface area contact and poor heat transfer characteristics.

To cool the skin while taking advantage of boiling at atmospheric pressure, one needs a liquid with a boiling point at atmospheric pressure below normal ambient temperatures. Heat from the skin boils these liquids. These refrigerant liquids are known and are used in air conditioning systems. Various fluorinated hydrocarbon fluids, such as those sold under the trademark Freon and mixtures of Freons, are known refrigerant liquids, and the present invention uses them. For cooling skin, the boiling point at standard pressure should be above 0° C. to prevent freezing of the skin. Liquids boiling below 0° C. could be used for cooling other objects.

In applicant's pending applications, localized cooling is used to cool a very small area of skin for a medical application. The cooling is accomplished by means of vaporization of a refrigerant liquid. The resultant gas is expelled to the atmosphere. The gas is costly and considered by some to pollute, and some have an offensive odor; it may be objectionable to vent the gas to the atmosphere, but these factors are minor in the medical device because it vents relatively small amounts of refrigerant gas. In a whole-body cooling apparatus, a much greater volume of gas would be lost, which raises the cost of each application. Therefore, it is an object of the present invention to disclose and to provide a localized cooling material in which the vaporized gas is not vented to the atmosphere.

Recycling the gas creates a problem. One cannot allow the gas to stay in the cooling device or the device quickly becomes pressurized and boiling efficiency drops dramatically. It is impractical and inefficient to repressurize the relatively small amount of low pressure gas immediately and direct it back to the storage tank. It is an object of the present invention, therefore, to disclose and provide a system for holding interim storage of the spent gas and injecting it back into the storage tank as a liquid.

For maximum efficiency and control, the liquid should remain liquid until it is in a location where the skin temperature causes it to boil. Premature boiling in feed lines wastes the cooling potential of the liquid. Both of the pending applications attempt to cause the injection of the liquid to take place in the cooling chamber to conserve the cooling potential of the liquid so that it is not wasted in the lines. Also, by causing only liquid to be injected into the cooling chamber, control may be maintained. It is an object of the present invention, therefore, to disclose and provide valves or other controllers as close to the cooling location as possible. In the medical devices, very precise temperature controls to $\pm 0.05°$ F. ($\pm 0.03°$ C. [metric equivalents are approximate]), may be needed. A cooling fabric would not have to cool in such precise increments. A $\pm 1°$ or $2°$ F. difference may be acceptable. Another object of this invention is to disclose and provide a relatively low-cost valve that can still be used to maintain the temperature control needed.

If the fabric covers wide areas of the body, it is desirable to be able to control those areas to effect different rates of cooling and different temperatures at localized sites. As a result, an additional object of the present invention is to design a valve that uses low power but is small and compact enough so that it can fit into the cooling fabric at one or several sites without being heavy, conspicuous and expensive.

Applicant's application Ser. No. 673,509 discloses (in somewhat schematic form) a cooling fabric which uses injectors disclosed in that application. It is an object of the present invention to improve on that system and utilize the fabric as a cooling chamber and to improve on the injectors themselves. These and other objects of the present invention will become evident from the following description of it.

SUMMARY OF THE INVENTION

The localized cooling device of the present invention comprises a bladder of flexible material. Inlet means extend from a source of refrigerant liquid into the bladder for transporting the refrigerant liquid under pressure. The refrigerant liquid boils at standard temperature and pressure. A valve at the end of the inlet means in the bladder releases the refrigerant liquid into the bladder whereby the liquid boils and cools the object against which the localized cooling device is against.

The device also includes a system for recycling spent gas. A low-pressure holding chamber collects the gas without causing objectionable pressure increases within the cooling chamber. A sensor determines when the holding chamber is sufficiently pressurized, and the sensor then starts a compressor to take the gas out of the holding chamber and to pressurize it, which returns the gas to its liquid stage. Pressurization increases the temperature of the fluid. A heat exchanger may be provided to cool the resultant liquid. The liquid then passes through a check valve back into the storage tank holding the liquid refrigerant.

The injector that is used comprises a relatively flat coil preferably on the upper portion of the cooling device. The inlet extends into a central chamber which is sealed by means of a steel or other magnetizable disk spring-loaded to the bottom of the chamber. When the solenoid is activated, the magnetic member tends to move toward the center of the coil against the spring load and exposes the outlet from the chamber. The liquid under pressure rushes past this outlet into the cooling fabric.

This fabric has several layers. The uppermost layer, which is above the injector, is formed of a thin, plastic membrane. There may be one or more outer layers on the upper portion of the thin plastic membrane to resist abrasion, reflect heat outward and insulate against heat loss. Liquid from the injector passes through high void plastic vapor passage material, one example of which is sold under the trademark Trilock. It allows the liquid to pass generally unimpeded. The liquid then strikes highly absorbent wicking materials so that it is transported over a wide area of the cooling fabric. Beneath this cooling device is another layer of the thin plastic membrane. This layer is heated by the skin, and the refrigerant boils from this layer. Heat is thus carried away from the skin in the gaseous state and as a result the skin cools.

A temperature sensor may also be provided above the lower membrane for sensing skin temperature or device temperature, and the temperature reading can be used in a feedback system for monitoring and controlling temperatures at various locations. An open-weave washable moisture absorbent material lies on the bottom of the lower membrane in contact with the skin (if the device is being used on the skin). This type of material enhances comfort and prevents one from feeling "clammy" when the device is cooling against the skin.

Quilting fasteners are spaced throughout the fabric to prevent ballooning of the garment due to the slight pressure of spent vapor. These quilting fasteners may be threads, rivets or even a heat-seal at selected locations.

BRIEF DESCRIPTION OF THE DRAWINGS

FIG. 1 is a side elevation, partially in section of the cooling fabric of the present invention.

FIG. 2 is a perspective view of a portion of the cooling fabric of the present invention.

FIG. 3 is a sectional view of a modification of the injector of the cooling fabric of the present invention.

FIG. 4 is a front sectional view of the injector used in the cooling fabric of the present invention.

DETAILED DESCRIPTION OF THE PREFERRED EMBODIMENTS

1. The Cooling Material

Figure 5:
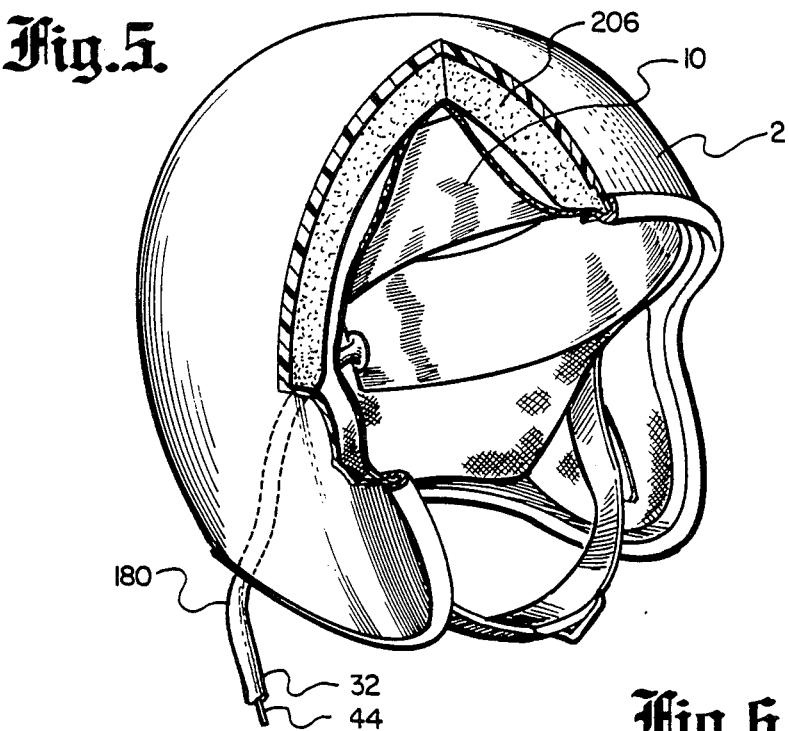
FIG. 5 shows the cooling device of the present invention mounted within a helmet.

Cooling fabric 10 of the present invention comprises a bladder of flexible material (FIGS. 1–4). In the exemplary embodiment, the bladder comprises an upper and lower thin plastic membranes 12 and 14 formed of heat sealable plastic such as nylon, PVC or Capton, although other materials that prevent liquids, especially refrigerant liquids, from passing through them and that allow heat flow are also acceptable. As will be explained in more detail, liquid refrigerant is injected onto wick 20 in cavity 16 formed between membranes 12 and 14.

When the cooling fabric is to be used against skin, it is desirable to have an open-weave, washable moisture absorbent material 18 (FIGS. 1–4) be interposed between lower membrane 14 and the skin. Moisture absorbent material 18 should be of a highly wettable fabric or of a paper having sufficient wet strength. The weave is sufficiently open so that the material does not act as an insulator. Its primary purpose is to absorb condensate from the outside of membrane 14 or to absorb perspiration from the skin. It is known that a very wide open weave is sufficient to prevent the device from feeling "clammy."

Wick 20, which may comprise one or more layers of highly absorbent material, is above lower membrane 14. Wick 20 is designed to distribute the liquid refrigerant to all interior surfaces of lower membrane 14 for balanced cooling along lower membrane 14. Temperature sensor 22 is interposed in the exemplary embodiment between lower membrane 14 and wick 20. The inside surface of sensor 22 may be thermally insulated so that it measures skin temperature primarily. Temperature sensor 22 is designed to read skin temperature and/or cooling fabric temperature. Microprocessor 202 (FIG. 6) reads the temperature and determines if and when additional refrigerant will have to be injected into cavity 16 for increased cooling. If the fabric is large enough in area, it is contemplated that there will be more than one injector and more than one temperature sensor. The microprocessor can be programmed to take the temperature information and balance the system or to insure that one area, which should be cooled to a greater degree, receives more refrigerant than other areas. The system's control is described below.

A high void plastic vapor passage, or 3-D material 24 (shown schematically without reference to its actual construction) is above wicking material 20. One acceptable material is sold under the trademark Trilock. 3-D material 24 allows spent refrigerant gas to flow generally freely in three directions from wick 20 and allows the gas to be ejected from the cooling material without an objectionable increase in gas pressure. 3-D material 24 gives body to the cooling fabric and causes the fabric to maintain dimensional stability, but it is also flexible so that the cooling member 10 can be bent in any reasonable shape to conform with the user's physique.

Edges 26 and 27 of membranes 12 and 14 are sealed so that cavity 16 is leak-proof. As shown in FIG. 1, one or more tubes 32 may pass through the portion where edges 26 and 27 are sealed together. In that area, edges 26 and 27 are sealed to the tube. Tube 32 and any other tube may also pass through upper or lower membrane 12 or 14 depending on the desired configuration of the cooling fabric.

Connecting means, which in the exemplary embodiment are small rivets 34, extend through upper and lower membranes 12 and 14 and any intermediate parts (e.g. 3-D material 24) to hold the membranes together so that the cooling fabric does not bulge greatly. Instead of a rivet, threads or other securing means may be used. If the system will be recycling spent refrigerant, any means for holding the membranes together will have to be sealed to prevent spent gas from leaking at the seal. The rivets or equivalents are spaced in a convenient pattern so that the material appears quilted.

One or more upper layers 28 (FIGS. 1 and 2) may cover upper membrane 12. Upper layer 28 may comprise one or more layers of material for abrasion resistance, heat insulation, protection from ire, reflection of radiant energy outward and protection from shock.

Upper membrane 12 may also have a coating of a material having a high emissivity coefficient. That is, the coating is designed to retain cold within cooling fabric 10 but to let heat radiate outward. The coating could also be a separate layer.

Injector 30 of the present invention is mounted within cavity 16 between membranes 12 and 14. As long as injector 30 directs refrigerant against wick 20 so that the refrigerant can cool the skin or other object, the placement of the injector is not critical. It may, for example, even outlet to a narrow diameter flexible hose having distribution hole(s) open toward wick 20. It is mounted within cavity 16 for protection, but it may be mounted apart from the rest of the cooling fabric for certain applications. The injector can be mounted above upper membrane 12, but a greater area of the upper membrane may have to be sealed, and the injector will be more easily dislodged.

In the exemplary embodiment, injector 30 is mounted on an annular shelf 36 (FIG. 1) such that there is an open space 21 (FIGS. 1–3) between injector 30 and wick 20. In FIG. 4, wick 20 is against modified injector 124. Without space 21 (FIG. 1) liquid is distributed more slowly. The diameter of space 21 can vary greatly. A small annular plate 38 (FIGS. 1 and 2) extends outward from top wall 40 of injector 30 and rests on part of 3-D material 24. Small holes 42 (FIG. 2) extend through annular plate 38 and allow the plate to be sewn to 3-D material 24. This secures injector 30 in its desired location and prevents the injector from drifting along the fabric during use.

An inlet line 44 and/or previously mentioned outlet line 32 also extend at least partially through cooling fabric 10 (FIGS. 1–3). The FIG. 4 embodiment is somewhat different and is discussed below. In FIG. 1, a narrow diameter inlet hose carrying liquid refrigerant under pressure extends between upper membrane 12 and protective layer 28, or as an alternative inlet hose 44 may run under membrane 12. As discussed in Ser. No. 673,509, the vaporization characteristics of Freon$_{114}$ make it ideal for skin cooling. As in the earlier application, the liquid may be pressurized by a higher vapor pressure refrigerant (e.g. Freon$_{12}$) acting through a piston or bladder on the Freon$_{114}$. The configuration of fitting 46 (FIGS. 1 and 3) or fitting 47 (FIG. 2) may be altered depending on locations of parts. In view of the small size of the fitting 46 or 47 and inlet tube 44, these items are barely noticed and are mere bumps on the outside of the fabric. If the cooling fabric is mounted within a hard object such as helmet 2 (FIG. 5), the inside surface of the helmet can have small, properly spaced indentations in the inside of the helmet to receive the small projection caused by the fittings.

It is anticipated that inlet line 44 either travels against outlet hose 32, or, as shown in the exemplary embodiment, narrow diameter inlet tube 44 is carried within wider diameter outlet tube 32 (FIG. 1 and schematically in FIG. 5). Electrical leads, such as lead 48 which carries the signal from temperature sensor 22 and leads 50 and 51 from valve 30 (FIG. 2), also are small enough to be carried within outlet hose 32. Of course, wherever electrical leads 48, 50 or 51 or inlet tube 44 pass through the outside of outlet tube 32, there must be a seal to prevent fluid or gas leakage.

2. The Injector

Co-pending application Ser. No. 673,509 discloses a miniature solenoid valve/injector. That valve would work in the present invention, and there is a disclosure in that application for one possible use of that valve in a cooling fabric. The shape of the valve is not ideal and it was designed to have a small cooling surface. The present invention utilizes a new injector, which was designed to be relatively flat so that it could be accommodated in the relatively flat cooling fabric of the present invention. The injector may take a number of forms. Two embodiments are shown in FIGS. 3 and 4; the FIG. 3 unit is described first.

Injector 30 has a flat, round, horizontal, electromagnetic coil 62 (FIGS. 1 and 3). The coil is surrounded by an annular plastic housing which includes an inner wall 64, top and bottom walls 66 and 68 (FIGS. 2 and 3), and end wall 70 (FIG. 1). Electric leads 50 and 51 (FIG. 2) extend to coil 62. The remaining parts of the injector are mounted at the center of coil 60.

Inside wall 64 defines central cavity 72 (FIG. 3), which is closed by wall 69. This wall is flush with bottom wall 68. The top of central cavity 72 is closed by cover 74 (FIGS. 2 and 3), which is threaded into the upper portion of central wall 64. Top wall 76 of cover 74 is flush with top wall 66 of coil housing 62 (FIG. 3). Outer flange 78 of top wall 76 is received in recess 80 of coil housing top wall 66, and is sealed by O-ring 82. Cover 74 also has a central threaded boss 84 (FIGS. 2 and 3). Fitting 46 is threaded into boss 84 and it compresses sealing washer 86.

A small recess 88 surrounds boss 80 and receives the top portion of helical spring 90 (FIG. 3). The other end of spring 90 pushes against spring support 92, which is received within the top part of central opening 94 of solenoid plunger 96. Iron or steel plunger 96 is the only part near electromagnetic coil 60 that has magnetic attraction. All other parts are designed for maximum magnetic coupling and minimum electrical energy use. A hat-shaped sealing member 98 of rubber or soft material extends partially into the bottom of central opening 94 of plunger 96 and is fixed to the plunger. The bottom of sealing member 98 rests on upstanding portion 100 and covers openings 102 extending through central portion 69 (FIG. 3). Openings 102, which carry liquid refrigerant to wick 20 and lower membrane 14, are angled so that the fluid will tend to be directed out from the center of injector 30 for more even cooling. The number of openings 102 (preferably three or four) is a matter of choice to affect the desired distribution.

Flexible gasket 106 is attached to plunger 96 to allow the plunger to move up and down and stay aligned within central cavity 72. Gasket 106 has an outside circumferential knob 108 retained within circumferential slot 110 by cover side wall 77. The bottom of spring support 92 holds inner knob 112 in circumferential slot 114 on the upper part of plunger 96. Gasket 106 has a series of circumferential, spaced openings 116 aligned with passage 118 between the outside of plunger 96 and the inside of coil central wall 64.

Liquid refrigerant from hose 44 (FIG. 3) flows through passage 120 of fitting 46 and fills cavity 72. The refrigerant then flows through openings 116 and fills space 118. The liquid at equilibrium is at the same pressure in supply tank 198 (FIG. 6) at the upstream end of hose 44 and in injector 30, and hose 44. The pressure chosen depends on the vapor pressure of the refrigerant and the maximum ambient temperature to which the tank will be exposed so that the refrigerant remains in its liquid state within tank 198, hose 44 and cavity 72.

3. Injector Operation

When injector 30 is off (i.e. coil 60 is not energized), spring 90 pushing against spring support 92 urges plugger 96 downward so that hat-like seal 98 covers and seals openings 102 and prevents the refrigerant in space 118 from flowing through the openings. When the injector is off, there is also a net pressure force down on plunger 96 because the combined area on the top of spring support 92 and gasket 106 exposed to the fluid pressure is greater than the area on the bottom of plunger 96. No upward pressure acts on the bottom of hat-like seal 98 because the seal is in contact with upstanding portion 100. Of course, there is no downward net pressure if plunger 96 is raised and the bottom of hat-like seal 98 is exposed to the fluid (disregarding pressure differences caused by fluid movement).

Plunger 96 moves upward a small distance tending to center itself in electromagnetic coil 60 when the coil is activated. The upward movement of plunger 96 moves seal 98 upward to uncover openings 102 and allows the refrigerant to be injected through the openings and against wick 20 where it spreads to be in contact with lower membrane 14.

The heat flux from normal skin temperature causes the liquid, which is now at approximately ambient pressure, to boil. The phase change of the liquid to a gas cools lower membrane 14 and the skin or other object being cooled. The change of phase requires a large heat flux, so the cooling effect is rapid and great. Because membrane 14 is very thin, high heat flux takes place through it. This high heat flux takes place over the entire surface area of membrane 14 because the entire surface contacts the skin.

One preferred refrigerant is a fluorocarbon refrigerant sold under the trademark Freon$_{114}$. Its boiling point at ambient pressure is approximately 4° C. That temperature would be the minimum temperature that the system and the object being cooled could attain. Using this refrigerant adds a safety factor. The system cannot go below the freezing point of water; it will not cause frostbite or damage the skin. Normal blood flow below the surface of the skin also tends to raise the skin temperature.

The system is designed to lower temperatures to a much smaller degree, well above 4° C. The object, at least insofar as human comfort is concerned, is to lower the skin temperature just enough to induce sufficient comfort and remove excess amounts of internal or external heat. Therefore, maintaining the cooling fabric in the range of approximately 21° C. (72° F.) is more than sufficient cooling. For many tasks, a higher temperature is adequate.

4. Alternate Injector

FIG. 4 shows an alternative embodiment for the injector of the present invention. It too includes a coil 126 mounted within annularly shaped coil housing 128. The housing has a central wall 130, top and bottom walls 132 and 134 and an outside wall (not shown), which have proper magnetic coupling.

Cap 136 is threaded into the top portion of central coil wall 130. Spring support 138 is threaded to the inside of cap 136 and extends generally across the top part of cavity 140, which is inside of inner coil wall 130. Spring support 138 does not seal the top of cavity 140; it has a central opening 142 through which the upper portion of fitting 144 extends.

Fitting 144 is threaded into opening 170, which extends through magnetic plunger 150. Flange 145 of fitting 144 secures washer 148 to plunger 150. Spring 146 extends between spring support 138 and washer 148 and is held by downward flange 139. Washer 148 also secures the center portion of bellows/diaphragm 152 to the top of plunger 150, and knob 154 of diaphragm 152 is held within notch 156 on the top of plunger 150 to secure the diaphragm. Diaphragm 152 also has an outer ring member 158, which is secured between the bottom of side walls 137 and the upper part of the side wall 160 of cup-shaped member 162. In the position shown in FIG. 4, much of the intermediate portion of diaphragm 152 rests in space 164.

Sealing member 168 of a soft material is in a recess of upstanding portion 166 of bottom wall 163. Bore 142 extending through fitting 144 carries pressurized liquid refrigerant from hose 44 (FIGS. 1 through 3 and 6). Spring 146 (FIG. 4) urges plunger 150 and fitting 144 downward against seal 168, which closes passage 142. In this closed position, which is shown in FIG. 4, no liquid refrigerant flows. When coil 126 is activated, the magnetic force tends to cause plunger 150 to move upwards and to become centered between the top and bottom of the coil. This movement creates a space between the bottom of fitting 172 and seal 168. Liquid refrigerant then flows through passage 144 to delivery chamber 172. The pressurized liquid then passes at a high velocity through multiple openings 174, which are spaced around and extend through the bottom wall 163 of cup-shaped member 162. The refrigerant reaches wick 20 and spreads along lower membrane 14 where it is vaporized. As an alternative, a single opening would replace multiple openings 174. This opening would dispense fluid to a small plastic hose (not shown) having many holes pointing toward wick 20.

In the FIG. 4 embodiment, it is desirable to minimize the volume in chamber 172. When plunger 150 moves down and seal 168 re-seals, there is a pressure drop in chamber 172 as the liquid flows through openings 174. As the pressure drops, there may be some boiling of the liquid within chamber 172. Minimizing the volume of he chamber minimizes the volume of liquid that boils in the chamber. One way to minimize the actual volume is to mount the inside of bellows/diaphragm 152 closer to the center of plunger 150 and to curve the top wall of the plunger (as partially shown at 176).

It is recognized that as plunger 150 moves vertically under the influence of the magnetic field, fitting 144 and hose 44 (not shown in FIG. 4) also move vertically. The actual movements, however, are minute and will not be noticeable.

Both injectors are thin so that they both take up little room in the cooling fabric. Each also permits fluid injection to take place right at wick 20 and lower membrane 14 so that the liquid is at its desired locations where it vaporizes for cooling. Also, because the refrigerant is at a high pressure, it flows at a high velocity through openings 102 (FIG. 3) or 174 (FIG. 4) which causes it to burst out of openings and spread along wick 120 and lower membrane 114. Several other variations on the injector of the present invention are possible which would stay within the scope of the invention of the injector.

Mounting the injector in the fabric maximizes the cooling capacity of the cooling fabric; all liquid boils along the lower membrane against the skin. In many applications, however, it may be acceptable to separate the injector from the rest of the cooling fabric. For example, in medical applications, the cooling fabric may be incorporated into a bandage. As the bandages must be changed regularly, it is desirable to have the cooling fabric be disposable. By having the injector out of the fabric, the injector can be saved. A quick-disconnect valve fitting may connect the tubing between the injector and the fabric to either.

Control of the injector is discussed in greater detail below.

5. Recycling System

Spent gas can be vented to the atmosphere. The injectors disclosed in pending application Nos. 343,004 and 673,509 vent refrigerant to atmosphere, and Pat. No. 3,479,838, which uses water because it operates in the vacuum of space, vents the water vapor to space. There are many reasons why one would not want to vent spent refrigerant gas back to the atmosphere, and the present invention is designed to recycle the- refrigerant.

Figure 6:
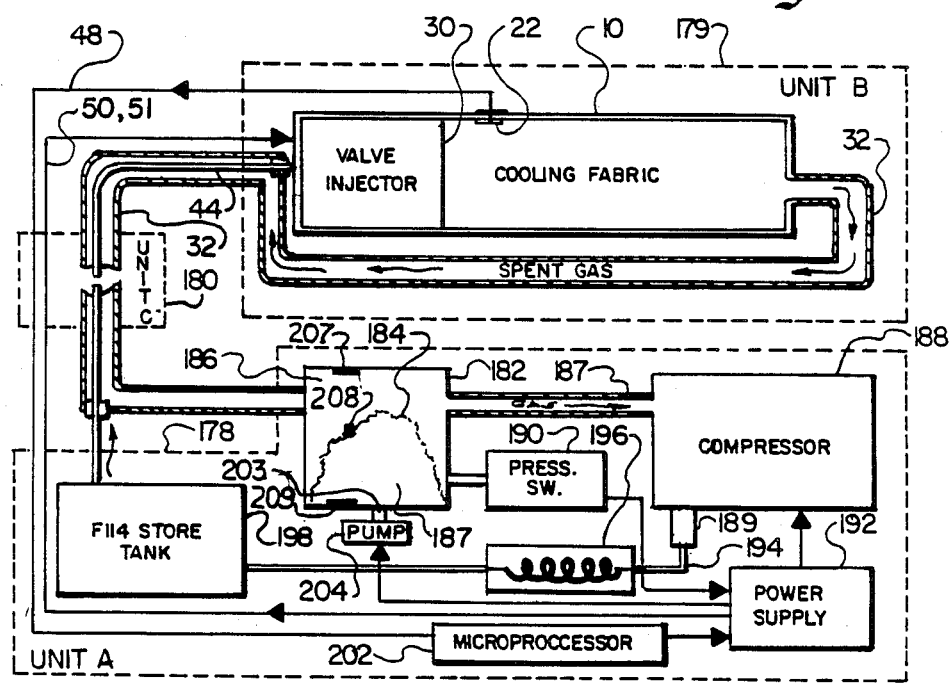
FIG. 6 is a schematic showing the closed cycle system of the cooling fabric of the present invention.

Referring to FIG. 6, there are three major parts of the recycling system for use with the cooling fabric. Unit A 178 consists mainly of the apparatus used to convert spent refrigerant gas back to liquid and to store the liquid under pressure. Unit B 179 is cooling fabric 10 and its injector valve 30. Unit C 180 is the interface between units A and B, the inlet and outlet hoses 44, 32 connecting units A and B together.

Spent refrigerant gas travels out through outlet hose 32 (FIGS. 1 and 6). Note that through a large part of the length of hose 32, inlet hose 44 travels inside or immediately adjacent the outlet hose. Gas from hose 32 flows into spent gas collector 182 within the A unit 178.

Spent gas collector 182 is designed for receiving and interim storage of the relatively low-pressure spent refrigerant gas from hose 32. A flexible bladder 184 (FIG. 6) is mounted within collector 182 and devices collector 182 into the regions, upper region 186 and lower region 187. The upper region 186 above bladder 184 is under a relatively low pressure. Lower portion 187 is vented to atmosphere. An alternative small pump 204 is discussed below. When the pressure in upper region 186 reaches a predetermined maximum because of gas build-up in spent gas collector 182, pressure switch 190 is activated to start compressor 188. Using latching type control, compressor 188 stays on until it causes pressure in upper region 186 of collector 182 to reach a set minimum, at which time switch 190 deactivates the compressor. Bladder 184 expands to minimize the volume of upper region 186. It is important not to raise the pressure in collector 182 much above ambient because the pressure would also be increased in hose 32 and in the cooling fabric, and that would cause boiling in the cooling to cease or decrease. The fabric would also bulge and be uncomfortable. Any negative pressure in collector 182 makes system cooling more effective.

Compressor 188 receives gas from spent gas collector 182 through tube 187. Although the compressor could run constantly and eliminate the need for spent gas collector 182, the compressor is actually compressing a small volume of gas at a relatively low pressure inlet to a high outlet pressure of about 60 psi or such other necessary pressure to cause the fluid to liquify. Even though the volume of gas may be relatively small, this type of compressor operation uses relatively large amounts of energy. The compressor should not run continuously and operates more efficiently at slightly higher pressures. Therefore, it is beneficial to collect the spent gas in collector 182 and operate compressor 188 intermittently. Pressure switch 190 reads the pressure in collector 182. When pressure switch 190 reads a predetermined pressure, it signals power supply 192 to activate the compressor. The compressor then takes gas in collector 182, pressurizes it and directs it out at a higher pressure through line 194. When the pressure in collector 182 drops below a predetermined minimum, pressure switch 190 signals power supply 192 to stop compressor 188. Check valve 189 is mounted at the outlet of compressor 188 before line 194 to prevent back flow of the pressurized fluid through compressor 188 to hose 32.

Lower region 187 of collector 182 can be vented to atmosphere at vent 203 (FIG. 6). As bladder 184 collapses from pressure of spent refrigerant gas in upper region 186, air is vented out vent 203. The vent may inlet to a low volume pump or compressor 204. Pump 204 is designed to pump air at only a slightly elevated pressure so that bladder 184 exerts a slight negative pressure on upper region 186. This negative pressure is present in the spent gas region upstream from collector 182, to minimize back pressure in cavity 16, 3-D material 24 and outlet tube 32 (FIG. 1) and prevents cooling fabric 10 from bulging.

Pump 204 can also evacuate refrigerant directly from line 32 and cooling fabric 10 and direct it to upper region 186 as a gas at only slightly elevated pressure. The effect on gas collection in collector 182 is similar to the effect that occurs if pump 204 were connected to lower region 187.

In FIG. 6, pressure switch measures pressure in upper region 186. Increased pressure causes changes in relative volumes between upper and lower regions 186 and 187. The pressure switch can be replaced with volume sensitive switches. FIG. 6 shows one possible arrangement. As gas from pump 204 fills upper region 186 (assuming the pump directs gas from line 32 to upper region 186), bladder 184 moves downward. Magnetic contact 208 contacts reed switch 209, which signals power supply 192 to latch on main compressor 188. The compressor runs continuously and evacuates upper region 186, which causes bladder 184 to move upward. When the bladder is in the upper-most position, contact 208 makes contact with switch 207, which signals the power supply to latch off the compressor. In this embodiment, spent gas collector 182 collects gas and acts as a pressure switch to latch compressor 188 on and off.

Bladder 184 is shown to be entirely flexible in FIG. 6. It may be replaced by a piston, bellows or similar member. These latter arrangements provide for better alignment of contact 208 as it moves between switches 207 and 209.

A second pump 204, which operates over a narrow pressure difference uses much less energy than compressor 188, which must pressurize refrigerant greatly. Power supply 192 powers pump 204. The pump may run continuously because it uses little energy, or a pressure switch or switches 207 and 209 may also control the pump.

Collector 182 is shown relatively small in the FIG. 6 schematic, but it must have sufficient volume to accommodate enough gas for its intended purpose. Any device which can expand to add volume without adding significantly to the pressure of the spent refrigerant may be used. The parts of the collector can be divided and located apart. For example, the upper region 186 could be in fabric 10.

When the pressure in upper region 186 of collector 182 is high enough and pump 204 has fully evacuated lower region 187, compressor 188 starts. The pressurization of the spent gas in compressor 188 raises the temperature of the fluid as it exits the compressor in line 194. A heat exchanger 196 is provided to cool the fluid. Upstream of heat exchanger 196 the fluid may be liquid or gas depending on its temperature. The heat exchanger is designed to remove the heat, and as it is mounted away from the skin or object to be cooled, the heat can be radiated or convected away without warming the person or object. Storage tank 198 receives liquid from heat exchanger 196 through line 200. Depending on the rate at which the system uses refrigerant and the size of tank 198, heat exchanger 196 may be optional; the tank may be made to radiate sufficient heat to cool the incoming pressurized fluid sufficiently.

The system uses small amounts of power. Therefore, it can be completely portable. Power supply 192 would then be a battery or other portable power supply. The power supply may also be through a power line attached to a more permanent power supply such as an A/C line into a factory power supply or electrical leads from a vehicle, aircraft, vessel or other mobile unit having electrical power. The compressor could also be clutch connected to a mechanical power takeoff from a motor or engine.

Although there are similarities between a typical refrigeration cycle and the operation of the recycling system of the present invention, certain important differences emerge. In a typical refrigeration system, cooling takes place only when the compressor is operating. In the present invention, the compressor only runs when the pressure in collector 182 exceeds a certain predetermined maximum above ambient. Cooling continues to take place as injector 30 carries liquid refrigerant from tank 198 through inlet hose 44 into the cooling fabric 10. Thus, unlike typical refrigeration systems, the system of the present invention has a volume absorber, collector 182. Likewise, in a typical refrigeration cycle, when the compressor is off, the pressures at the inlet and outlet to the compressor are the same. Check valve 189 maintains the pressure at the outlet to compressor 188 at a much higher pressure than the inlet pressure from line 187.

6. Helmet

One potential application for the cooling fabric of the present invention is as a lining to a helmet, in this case, a motorcycle or race driver's helmet. Cooling fabric 10 is placed in a desired pattern on the inside of helmet 2 (FIG. 5). It would cooperate with padding 206 necessary for head protection. Inlet line 44 traveling within outlet line 32 is shown extending down out of the back of the helmet. If the cooling fabric has more than one injector, there is either multiple inlet and outlet hoses, or the main hoses branch. As an alternative, only the inlet lines have to branch as long as there is sufficient volume in the outlet line(s) to carry away the spent gas without causing the pressure within the cooling fabric to rise significantly.

Electrical leads 50 and 51 leading to injectors 30 and the electrical lead 48 leading from temperature sensor 22 also travels either inside outlet tube 32 or immediately adjacent the outside of the tube. This is shown schematically in FIG. 6 where lines 48, 50 and 51 pass through the C unit 180.

Power supply 192 also activates injector 30 through lines 50 and 51 in response to temperature signals from temperature sensor 22, electrical lead 48 and microprocessor 202, which controls power supply 192. Modifying the fabric for larger garments is a matter of sewing and depends on the size of standard pieces of fabric that are being manufactured. Larger sizes can be formed into a vest or a whole body suit. The size of the components in the A unit 178 must be modified to handle the larger volume of refrigerant, but the operating principal should be the same.

Various modifications and changes may be made in the configuration described above that come within the spirit of this invention. The invention embraces all such changes and modification coming within the scope of the appended claims.

I claim:

1. A localized cooling device comprising:
   membrane means of flexible material for forming a cavity;
   inlet means extending into the cavity for transporting a pressurized refrigerant liquid, which boils at standard pressure and temperature; and
   injector means at the end of the inlet means inside of the cavity for controlled release of refrigerant liquid in the cavity whereby the liquid boils and becomes gas from heat flux from the membrane which in turn cools the membrane and any object in contact with it.

2. The localized cooling device of claim 1 wherein the injector means comprises an annular electromagnetic coil, which surrounds a central chamber, the inlet means extending into the central chamber and carrying the refrigerant liquid into the central chamber, the central chamber having opening means extending from the central chamber into the cavity for importing the refrigerant liquid into the cavity, plunger means including sealing means normally biased over the opening means for blocking the flow of refrigerant liquid from the inlet means to the cavity, the plunger means moving to an open position in response to magnetic force from the electromagnetic coil for uncovering the opening means and permitting fluid to flow through the openings into the cavity.

3. The localized cooling device of claim 2 wherein the plunger means is normally mounted at one end axially of the central chamber, the magnetic force tending to center the plunger means axially.

4. The localized cooling device of claim 3 further comprising centering means attached to the plunger means for maintaining the plunger means on its axis of movement.

5. The localized cooling device of claim 4 further comprising passage means extending between the inside of the central chamber and the outside of the plunger means for conducting refrigerant liquid from the inlet means to the opening means, the centering means having openings aligned with the passage means for permitting liquid to flow into the passage means.

6. The localized cooling device of claim 3 wherein the plunger means has a plunger passage aligned with the inlet means, the sealing means blocking the plunger passage when the plunger means is in its normal position, a chamber passage between the plunger passage and one wall of the chamber, the one wall of the chamber having openings which extend into the cavity, movement of the plunger means to the open position in response to magnetic force from the electromagnetic coil moving the sealing means away from the chamber passage to permit refrigerant liquid to flow from the plunger passage through the chamber passage to the opening means.

7. The localized cooling device of claim 6 further comprising centering means attached to the plunger means for maintaining the plunger means on its axis of movement and for closing the chamber passage.

8. The localized cooling device of claim 1 wherein the inlet means is connected to a source of pressurized refrigerant liquid, recycling means extending through the membrane means for carrying spent refrigerant gas out of the cavity and returning it to the source.

9. The localized cooling device of claim 8 wherein the recycling means comprises an outlet for transporting the spent refrigerant gas from the cavity, a compressor for receiving the spent gas from the outlet and increasing the pressure of the gas and tank inlet means extending between the compressor and the source of refrigerant liquid the recycling means further comprising spent gas collector means between the outlet, and the compressor for collecting gas at low pressure.

10. The localized cooling device of claim 9 wherein the spent gas collector means comprises a chamber and a bladder attached to the inside of the chamber dividing the spent gas collector means into two volumes, a first volume being sealed by the bladder and a second volume receiving spent gas from the outlet to collapse the bladder.

11. The localized cooling device of claim 10 further comprising switch means in the spent gas collector means for determining the relative pressures between the first and second volumes and means for connecting the switch means to the compressor for activating the compressor when the pressure difference between the first and second volumes reaches a predetermined first pressure difference and for stopping the compressor when the pressure difference between the first and second volumes reaches a predetermined second pressure difference.

12. The localized cooling device of claim 10 further comprising switch means in the spent gas collector means for determining the relative volumes between the first and second volumes and means for connecting the switch means to the compressor for activating the compressor when the volume difference between the first and second volumes reaches a predetermined first volume difference and for stopping the compressor when the volume difference between the first and second volumes reaches a predetermined second volume difference.

13. The localized cooling device of claim 12 wherein the switch means comprises a first switch in the first volume and a second switch in the second volume, contact means attached to the bladder moving between the first and second switches to signal the compressor for activating the compressor when the contact means activates one of the switches and for stopping the compressor when the contact means activates the other switch.

14. The localized cooling device of claim 10 further comprising check valve means between the compressor and the source of refrigerant liquid for preventing liquid from flowing from the source back through the compressor.

15. The localized cooling device of claim 10 further comprising a heat exchanger between the compressor and the source of liquid for expelling heat added to the refrigerant liquid during pressurization in the compressor.

16. The localized cooling device of claim 10 further comprising a second compressor means attached to the first volume of the spent gas collector for decreasing the pressure in the first volume.

17. The localized cooling device of claim 10 further comprising a second compressor attached to the second volume of the spent gas collector means for evacuating the spent gas from the cavity and for pressurizing the second volume.

18. The localized cooling device of claim 10 further comprising a vent from the first volume of the spent gas collector means to atmosphere for venting pressure in the first volume.

19. An injector for injecting fluid into a container comprising an annular electromagnetic coil, which surrounds a central chamber, the inlet means extending into the central chamber and carrying the fluid into the central chamber, the central chamber having opening means extending from the central chamber into the cavity for importing the fluid into the cavity, plunger means including sealing means normally biased over the opening means for blocking the flow of fluid from the inlet means to the cavity, the plunger means moving to an open position in response to magnetic force from the electromagnetic coil for uncovering the openings and permitting fluid to flow through the openings into the cavity.

20. The injector of claim 19 wherein the plunger means is normally mounted at one end axially of the central chamber, the magnetic force tending to center the plunger axially.

21. The injector of claim 20 further comprising centering means attached to the plunger means for maintaining the plunger means on its axis of movement.

22. The injector of claim 21 further comprising passage means extending between the inside of the central chamber and the outside of the plunger means for conducting the fluid from the inlet means to the opening means, the centering means having openings aligned with the passage means for permitting the fluid to flow into the passage means.

23. The injector of claim 20 wherein the plunger means has a plunger passage aligned with the inlet means, the sealing means blocking the plunger passage when the plunger means is in its normal position, chamber passage means between the plunger passage and one wall of the chamber, the one wall of the chamber having openings which extend into the cavity, movement of the plunger means to the open position in response to magnetic force from the electromagnetic coil moving the sealing means away from the chamber passage to permit the fluid to flow from the plunger passage through the chamber passage to the openings.

24. The injector of claim 23 further comprising centering means attached to the plunger means for maintaining the plunger means on its axis of movement and for closing the chamber passage.

25. The injector of claim 19 wherein the inlet means is connected to a source of pressurized fluid recycling means extending through the membrane means for carrying spent fluid out of the cavity and returning it to the source.

* * * * *